United States Patent [19] [11] Patent Number: 4,981,682
Boothroyd et al. [45] Date of Patent: Jan. 1, 1991

[54] DEPILATORY COMPOSITIONS

[75] Inventors: Stephen Boothroyd, Nottingham; Christine Sheard, Long Eaton, both of England

[73] Assignee: The Boots Company PLC, England

[21] Appl. No.: 494,882

[22] Filed: Mar. 9, 1990

Related U.S. Application Data

[63] Continuation of Ser. No. 239,505, Sep. 1, 1988, abandoned.

[30] Foreign Application Priority Data

Sep. 5, 1987 [GB] United Kingdom ............... 8720937

[51] Int. Cl.$^5$ ............................................. A61K 7/09
[52] U.S. Cl. ........................................ 424/72; 8/160; 8/161; 424/70; 424/71; 424/73
[58] Field of Search .................... 424/70, 71, 72, 73; 8/160, 161

[56] References Cited

U.S. PATENT DOCUMENTS

| | | | |
|---|---|---|---|
| 3,154,470 | 10/1964 | Braun et al. | 8/161 |
| 4,121,904 | 10/1978 | Schamper | 8/161 |
| 4,579,131 | 4/1986 | Syed | 132/202 |
| 4,618,344 | 10/1986 | Wells | 8/161 |

FOREIGN PATENT DOCUMENTS

| | | |
|---|---|---|
| 62372 | 10/1982 | European Pat. Off. |
| 155806 | 9/1985 | European Pat. Off. |
| 2204398 | 5/1974 | France. |
| 57908 | 2/1969 | Luxembourg. |

*Primary Examiner*—Lester L. Lee
*Assistant Examiner*—Avis M. Davenport
*Attorney, Agent, or Firm*—Ostrolenk, Faber, Gerb & Soffen

[57] ABSTRACT

A depilatory composition comprising a depilatory compound, in particular potassium thioglycolate, and a tertiary amine of general formula I $$NR_1R_2R_3 \qquad I$$

wherein $R_1$ represents a long chain fatty moiety having 8 to 36 carbon atoms and $R_2$ and $R_3$ each independently represent a fatty moiety having 1 to 36 carbon atoms. The composition has pH of between 11.5 and 12.7. The softening effect of the tertiary amine avoids the growth of stiff stubble and does not reduce the efficacy of the depilatory compound.

12 Claims, No Drawings

DEPILATORY COMPOSITIONS

This is a continuation of application Ser. No. 239,505, filed on Sept. 1, 1988, now abandoned.

This invention relates to compositions useful for removing unwanted hair from the body.

Conventional depilatory compositions, usually in the form of a cream, are applied to the skin of the body at an appropriate place and after 5 to 15 minutes the cream is removed by means of a spatula, cotton wool, sponge or some other suitable material which is wiped over the skin. The active ingredient of such depilatory compositions is usually an alkali or alkaline earth metal salt of an alpha or beta mercaptocarboxylic acid, e.g. potassium or calcium thioglycolate. The active ingredient penetrates the hair and destroys the cysteine bonds between the hair molecules thus weakening the hair to such an extent that merely scraping or wiping the cream off the skin breaks the hair at skin level and thus removes it. The cream has to be used at a pH of 12 to 12.5 so that the active ingredient e.g. potassium thioglycolate can penetrate the hair and thus weaken the hair structure. The skin has a self-regulating system which restores the pH to the normal range of 5 to 7, usually 5.5 plus or minus 0.5 and any hair which is just below the surface of the skin which has been attacked by the active ingredient will then revert to its normal structure and strength as the cysteine bonds are reformed. Subsequent growth of the hair thus causes it to emerge as a stiff stubble shortly after treatment. The initial growth of such stubble can be uncomfortable in certain areas of the body particularly where the medical condition of Pseudofolliculitis exists and this discomfort is only relieved after a further day or so as the hair grows longer and more supple. The initial stiff stubble is also inconvenient because it can snag on fine fabric in clothing.

We have now discovered a depilatory composition which, whilst successful in removing unwanted body hair, substantially avoids the growth of stiff stubble.

Hair conditioning compounds such as those containing long chain fatty moieties, which impart smoothness and shine to hair, are well known. However, many of the known compounds are cationic and cannot be used in compositions having a pH of 12 or more. Others will break down at this pH, for example fatty acid esters will hydrolyse and quaternary ammonium compounds will revert to free amines. Furthermore, other known conditioning compounds cannot be used in depilatory compositions because they coat the hairs and thereby reduce the effective action of the depilatory compound. Surprisingly, we have now prepared depilatory compositions containing compounds which are stable at pH 12, which do not reduce the efficacy of the depilatory compound and which are capable of acting as hair conditioners.

Thus, according to the present invention, there is provided a depilatory composition comprising a depilatory compound and a tertiary amine of general formula I

$$NR_1R_2R_3 \qquad I$$

wherein $R_1$ represents a long chain fatty moiety having 8 to 36 carbon atoms and $R_2$ and $R_3$ each independently represent a fatty moiety having 1 to 36 carbon atoms, said composition having a pH of between 11.5 and 12.7. Preferably said composition has a pH of between 12 and 12.5.

The term "fatty moiety" as used herein denotes a hydrocarbon chain which may be derived from a fatty acid. The hydrocarbon chain may be a branched or unbranched aliphatic group, which may be saturated or unsaturated, or an aromatic group and may be optionally substituted for example with one or more hydroxy groups. Preferred fatty moieties are alkyl groups having 1 to 4 carbon atoms, for example methyl, or long chain fatty moieties which may be derived from naturally occurring fats and fatty acids, in particular straight chain saturated or unsaturated aliphatic groups having 8 to 36 carbon atoms, more particularly 16 to 24 carbon atoms.

Particularly preferred amines of formula I are those wherein at least two of the groups $R_1$, $R_2$ and $R_3$ each independently represent a straight chain aliphatic group having 16 to 24 carbon atoms, for example di(hardtallow)methylamine, distearylmethylamine and tri(hardtallow)amine.

The amines of formula I are not generally active as conditioning agents in compositions having a pH of 12 or above such as is found in conventional depilatory compositions but they do become cationic and hence effective at lower pH's, for example at a pH of 11.5 or less. However, the use of di- and tri- long chain fatty amines of formula I is preferred and these have been found to quickly become substantive by virtue of their effective pH range of 11.5 to 6.5 (depending on the specific amine used). Particularly preferred amines of formula I become cationic at a pH of between 8 and 11.

When a depilatory composition containing at least one amine of formula I is applied to skin, the composition penetrates the hair follicles and when the composition is wiped off after a suitable period of time the hair external to the skin is removed. The hair follicle below skin level retains the depilatory composition even when the skin is washed with water and the skin pH reverts naturally to a normal pH of 5.5 plus or minus 0.5. The hair thus regains its strength as the cysteine bonds are reformed but is conditioned by the amine of formula I as it becomes cationic and hence substantive and the hair subsequently grows out following the treatment without the formation of a stiff stubble.

Thus, a further aspect of the invention provides a method of removing hair from the body and substantially precluding the growth of a stiff stubble which comprises applying a depilatory composition according to the invention to the skin at an appropriate part of the body, leaving the composition in contact with the skin until the hair is adequately penetrated, usually 5–15 minutes, and then removing the composition from the surface of the skin.

The compositions of the invention may contain varying quantities of an amine compound of formula I in order to give the desired softness of regrowth. Using the novel compositions of this invention we have found that the optimum amount of amine of formula I in the compositions to preclude any substantial growth of stiff stubble is 1 to 10% w/w preferably around 5% w/w.

The depilatory compound may be, for example, an alkali or alkaline earth metal salt of an alpha or beta mercaptocarboxylic acid, preferably potassium or calcium thioglycolate. Varying quantities of the depilatory compound may be used for example between 3% and 10% w/w.

The depilatory compositions of the present invention may take the form of any of the known depilatory compositions, for example creams, lotions or aerosols and may be prepared using conventional methods known in the art. In addition to a depilatory compound and a tertiary amine of formula I, compositions according to the invention may contain other components which will be well known to those skilled in the art, for example emolients such as cetyl alcohol, liquid paraffin or white soft paraffin, humectants such as urea or 1,3-butylene glycol, emulsifying agents such as ethoxylated cetyl or stearyl alcohol, antioxidants such as butylated hydroxytoluene, thickeners such as sodium magnesium silicate, sequestrants such as sodium heptonate, stabilisers such as sodium metasilicate, or perfumes.

The efficacy of the depilatory compositions described herein may be objectively evaluated in skin substantivity tests. Samples of a depilatory composition according to the invention and a control depilatory composition (containing no amine of formula I) are applied to adjacent areas of skin for a suitable period of time, for example 5 to 7 minutes, before being wiped off and the area rinsed well with tap water. At appropriate intervals thereafter the entire area may be treated with a suitable anionic dye, for example the ultra violet fluorescent dye Tinopal CBS-X (trade name of Ciba Geigy, England), in order to locate any cations remaining bound to the skin or the hair. Compositions according to the present invention are found to deposit cations which remain bound to the skin and in particular to the tips of growing hairs for up to one week after treatment in contrast to control compositions which leave no substantial cationic deposit on the skin or hair 24 hours after treatment.

The invention is illustrated by the following Examples which are not intended to limit the invention in any way.

In the Examples, sodium magnesium silicate was obtained from Laporte Industries, England, under the trade name Laponite XLS; di(hardtallow)methylamine from Akzo Chemie UK Ltd, England, under the trade name Armeen M2HT; distearylmethylamine from S.A. Synfina Oleofina N.V., Belgium, under the trade name Radiamine 6346; propellant from ICI, England, under the trade name Arcton 12/114 40/60; ethoxylated cetyl alcohol from Croda, England under the trade name Cetomacrogol 1000 BP; and $Fe^{3+}$ sequestrant from W R Grace Inc. USA, under the trade name Detarex HM.

EXAMPLE 1

| Depilatory Cream | % w/w |
|---|---|
| Sodium magnesium silicate (Laponite XLS) | 2 |
| Sodium heptonate | 0.25 |
| Water | to 100 |
| Cetyl alcohol | 6 |
| Ethoxylated cetyl alcohol (Cetomacrogol 1000 BP) | 3 |
| Light liquid paraffin | 2.5 |
| 3 mol ethoxylated stearyl alcohol | 0.5 |
| Butylated hydroxytoluene | 0.1 |
| Di(hardtallow)methylamine (Armeen M2HT) | 5 |
| Potassium thioglycolate (42%) soln. | 10 |
| Calcium hydroxide | 3 |
| Urea | 5 |
| Perfume | 0.5 |

(Cetyl alcohol through Di(hardtallow)methylamine grouped as A)

Method (a) disperse the sodium magnesium silicate and sodium heptonate in water at 70° C.;
(b) heat constituents of A to 70° C. with mixing;
(c) add b to a and homogenize;
(d) cool to 30° C., add potassium thioglycolate and calcium hydroxide;
(e) add urea and perfume.

EXAMPLE 2

| Depilatory Lotion | % w/w |
|---|---|
| Cetyl alcohol | 5 |
| 20 mol ethoxylated stearyl alcohol | 2 |
| Light liquid paraffin | 1 |
| Distearylmethylamine (Radiamine 6346) | 5 |
| 1,3-Butylene glycol | 1 |
| $Fe^{3+}$ sequestrant (Detarex HM) | 0.1 |
| Potassium thioglycolate soln. (42%) | 14 |
| Calcium hydroxide | 0.5 |
| Potassium hydroxide | to pH 12.5 |
| Perfume | 0.5 |
| Water | to 100% |

(Cetyl alcohol through Distearylmethylamine grouped as A)

Method (a) heat constituents of A to 70° C. with mixing;
(b) heat water, $Fe^{3+}$ sequestrant and 1,3-butylene glycol to 70° C.;
(c) add a to b with homogenization;
(d) disperse calcium hydroxide in a little water and add to c.
(e) cool to 30° C., add potassium thioglycolate soln. and adjust pH to 12.5 with potassium hydroxide;
(f) add perfume.

EXAMPLE 3

| Depilatory (Aerosol Formulation) Concentrate | % w/w |
|---|---|
| Water | to 100% |
| Tri(hardtallow)amine | 5 |
| Liquid paraffin BP | 3 |
| 20 mol ethoxylated cetyl alcohol | 1.5 |
| Cetyl alcohol | 0.5 |
| White soft paraffin | 3 |
| Sodium metasilicate | 0.5 |
| Potassium thioglycolate (42%) soln. | 14 |
| Calcium hydroxide | 0.5 |
| Potassium hydroxide | to pH 12.5 |
| Perfume | 0.5 |

(Tri(hardtallow)amine through White soft paraffin grouped as A)

Method (a) dissolve sodium metasilicate in water at 70° C.;
(b) heat constituents of A to 70° C. with mixing;
(c) add b to a and homogenize;
(d) cool to 30° C. and add potassium thioglycolate;
(e) add calcium hydroxide and disperse;
(f) add potassium hydroxide to pH 12.5;
(g) add perfume.

Aerosol can fill:

| Concentrate | 85% w/w |
|---|---|
| Arcton 12/114 40/60 | 15% w/w |

Any suitable aerosol can, valve or actuator can be used. The propellant can also be hydrocarbon eg butane, dimethyl ether or blends.

What is claimed is:

1. A depilatory composition comprising from 3 to 10% w/w of a depilatory compound selected from the group consisting of alkali and alkaline earth metal salts of alpha and beta mercaptocarboxylic acids and from 1 to 10% w/w of a tertiary amine of general formula I $$NR_1R_2R_3 \qquad I$$

wherein $R_1$ represents a long chain fatty moiety having 8 to 36 carbon atoms and $R_2$ and $R_3$ each independently represent a fatty moiety having 1 to 36 carbon atoms, said composition having a pH of between pH 11.5 and 12.7.

2. A depilatory composition as claimed in claim 1 having a pH of between 12 and 12.5.

3. A depilatory composition as claimed in claim 1 wherein $R_1$ represents a straight chain aliphatic group having 8 to 36 carbon atoms and $R_2$ and $R_3$ each independently represent an alkyl group having 1 to 4 carbon atoms or a straight chain aliphatic group having 8 to 36 carbon atoms.

4. A depilatory composition as claimed in claim 1 wherein at least two of the groups $R_1$, $R_2$ and $R_3$ each independently represent a straight chain aliphatic group having 16 to 24 carbon atoms.

5. A depilatory composition as claimed in claim 1 wherein the tertiary amine of formula I is di(hardtallow)methylamine, distearylmethylamine, or tri(hardtallow)amine.

6. A depilatory composition as claimed in claim 1 which is in the form of a cream, lotion or aerosol.

7. A depilatory composition as claimed in claim 1 wherein the depilatory compound is potassium or calcium thioglycolate.

8. A method of removing hair from the body and to give re-growth of hair following treatment without the formation of a stiff stubble which comprises applying a depilatory composition as claimed in claim 1 to the skin at an appropriate part of the body, leaving the composition in contact with the skin until the hair is adequately penetrated, and then removing the composition from the surface of the skin.

9. A depilatory composition as claimed in claim 7 having a pH of between 12 and 12.5.

10. A depilatory composition as claimed in claim 9 wherein at least two of the groups $R_1$, $R_2$ and $R_3$ each independently represent a straight chain aliphatic group having 16 to 24 carbon atoms.

11. A depilatory composition as claimed in claim 10 wherein the tertiary amine of formula I is di(hardtallow)methylamine, distearylmethylamine, or tri(hardtallow)amine.

12. The method of claim 8 in which the composition is left in contact with the skin for 5 to 15 minutes.

* * * * *